United States Patent
Pilgrim et al.

(10) Patent No.: US 6,618,148 B1
(45) Date of Patent: Sep. 9, 2003

(54) ACOUSTIC RESONANCE FREQUENCY LOCKED PHOTOACOUSTIC SPECTROMETER

(75) Inventors: Jeffrey S. Pilgrim, Santa Fe, NM (US); David S. Bomse, Santa Fe, NM (US); Joel A. Silver, Santa Fe, NM (US)

(73) Assignee: Southwest Sciences Incorporated, Santa Fe, NM (US)

( * ) Notice: Subject to any disclaimer, the term of this patent is extended or adjusted under 35 U.S.C. 154(b) by 0 days.

(21) Appl. No.: 09/782,138

(22) Filed: Feb. 12, 2001

Related U.S. Application Data
(60) Provisional application No. 60/181,610, filed on Feb. 10, 2000.

(51) Int. Cl.[7] .............................................. G01N 21/00
(52) U.S. Cl. ................... 356/432; 356/437; 250/339.09
(58) Field of Search .......................... 356/432, 437, 356/441; 250/343, 339.07, 339.09; 73/24.02; 359/134

(56) References Cited

U.S. PATENT DOCUMENTS

| | | | | |
|---|---|---|---|---|
| 3,938,365 A | * | 2/1976 | Dewey, Jr. .................. | 73/24.02 |
| 4,051,371 A | * | 9/1977 | Dewey, Jr. et al. ...... | 250/339.09 |
| 4,051,372 A | * | 9/1977 | Aine .......................... | 250/343 |
| 4,200,399 A | * | 4/1980 | Kimble et al. .............. | 356/437 |
| 4,533,252 A | * | 8/1985 | Cahen et al. ................ | 356/432 |
| 4,633,524 A | * | 12/1986 | Hasegawa .................... | 359/134 |
| 4,738,536 A | * | 4/1988 | Kitamori et al. ............ | 356/441 |
| 5,120,961 A | * | 6/1992 | Levin et al. ........... | 250/339.07 |
| 5,129,255 A | * | 7/1992 | Corbin ....................... | 73/24.02 |
| 5,159,411 A | * | 10/1992 | Hammerich et al. ........ | 356/432 |

FOREIGN PATENT DOCUMENTS

JP        9-133655 A    *  5/1997

OTHER PUBLICATIONS

Angeli, G.Z., et al., "Design and Characterization of a Windowless Resonant Photoacoustic Chamber Equipped with Resonance Locking Circuitry," *Rev. Sci. Instrum.*, vol. 62,k pp 810–813 (Mar. 1991).

Thony, A., et al., "New Developments in $CO_2$–Laser Phoacoustic Monitoring of Trace Gases," *Infrared Phys. Technol.*, vol. 36, pp 585–615 (1995). No month available.

Pao, Y–H, editor *Optoacoustic Spectroscopy and Detection*, Academic Press, New York 1997, pp 20–22, No month available.

* cited by examiner

*Primary Examiner*—Michael G. Lee
*Assistant Examiner*—Jared J. Fureman
(74) *Attorney, Agent, or Firm*—Jeffrey D. Myers

(57) ABSTRACT

A photoacoustic spectroscopy method and apparatus for maintaining an acoustic source frequency on a sample cell resonance frequency comprising: providing an acoustic source to the sample cell, the acoustic source having a source frequency; repeatedly and continuously sweeping the source frequency across the resonance frequency at a sweep rate; and employing an odd-harmonic of the source frequency sweep rate to maintain the source frequency sweep centered on the resonance frequency.

25 Claims, 2 Drawing Sheets

ACOUSTIC RESONANCE FREQUENCY LOCKED PHOTOACOUSTIC SPECTROMETER

CROSS-REFERENCE TO RELATED APPLICATIONS

This application claims the benefit of the filing of U.S. Provisional Patent Application Ser. No. 60/181,610, entitled "Acoustic Resonance Frequency Locked Photoacoustic Spectrometer", filed on Feb. 10, 2000, and the specification thereof is incorporated herein by reference.

A related application entitled "Acoustic Resonance Phase Locked Photoacoustic Spectrometer" is being filed concurrently herewith, to Jeffrey S. Pilgrim et al., U.S. patent application Ser. No. 09/782,137, and the specification thereof is incorporated herein by reference.

GOVERNMENT RIGHTS

The U.S. Government has a paid-up license in this invention and the right in limited circumstances to require the patent owner to license others on reasonable terms as provided for by the terms of Contract No. DE-FG03-99ER82887 awarded by the U.S. Department of Energy and of Grant No. DMI-9983349 awarded by the U.S. National Science Foundation.

BACKGROUND OF THE INVENTION

1. Field of the Invention (Technical Field)

The present invention relates to high-sensitivity detection of contaminants in gases by optical techniques generally termed photoacoustic spectroscopy (PAS) or optoacoustic spectroscopy.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Photoacoustic spectroscopy is a known technique for high sensitivity detection of trace gases. Absorption by the target species of incident optical energy results in a transient heating of the gas. If the incident optical energy is modulated then the gas is periodically heated which creates a time-varying pressure wave or sound. The sound can be measured with a microphone.

PAS is often enhanced through the use of acoustically resonant gas cells. These cells build up sound intensity at the resonance frequencies. Depending on the type of noise dominant in the system, resonant cells can dramatically improve signal-to-noise ratios and thereby, the measurement sensitivity. Individual and combination acoustic resonance modes including longitudinal, radial, and azimuthal are often utilized. Unfortunately, resonance frequencies depend on the local speed of sound which can change with temperature and gas composition. In addition, changes in cell dimensions due to mechanical stress can change these resonance frequencies. Thus, for a practical resonance-based photoacoustic spectrometer, it is necessary to maintain the modulation frequency at the acoustic resonance frequency.

The ability to maintain the optical source modulation frequency or its harmonics on an acoustic resonance frequency of a photoacoustic cell will hereafter be referred to as resonance frequency locking. In field measurements, microphone noise is not usually a photoacoustic instrument's sensitivity-limiting noise source. When microphone noise is not the limiting noise source, operation on an acoustic resonance enhances the signal-to-noise ratio. *Optoacoustic Spectroscopy* and Detection, Y-H Pao, ed. (Academic Press, New York, 1977), pps. 20–22. Because there is a 1/f dependence of the photoacoustic signal on frequency, operation at a resonance frequency represents a compromise between the enhancement, or Q, of the resonance cell and higher frequency operation. Thus, resonant operation is usually desirable provided the resonance frequency is not so high that the 1/f penalty outweighs the cavity Q. For example, a cell with a resonance at 8000 Hz with a Q of 200 would generate the same signal, all other parameters being equal, as a non-resonant cell operating at 40 Hz. In many systems, there is less background acoustic noise at 8000 Hz than at 40 Hz; resonant operation at 8000 Hz then provides a better signal-to-noise ratio.

Acoustic resonances may have narrow bandwidths. As the amplification factor (or resonance cavity Q) increases for a given frequency, the bandwidth gets narrower. Thus, as sensitivity is increased by improving the acoustic quality of the photoacoustic cell, the need for a method to maintain the acoustic modulation frequency on resonance increases proportionately. For example, a cell with a Q of 200 at 8000 Hz will have a bandwidth of 40 Hz. Thus, a change of the resonance frequency of only 20 Hz will reduce the signal by a factor of 2. A change of 20 Hz can be caused by a temperature change of less than 1 degree C at room temperature.

The present invention achieves continuous, real-time acoustic resonance frequency locking by sweeping the optical source modulation frequency or its harmonics across a cell acoustic resonance. Because the frequency of the modulation is swept over the cell resonance, the amplitude of the acoustic signal is modulated. The acoustic resonance converts the frequency modulation into an amplitude modulation. This effect is similar to frequency or wavelength modulation where a laser is swept across a molecular absorption feature where there is a maximum attenuation of the beam on the peak of the molecular absorption. With the present invention, there is a maximum amplification or enhancement on the peak of the acoustic resonance feature.

With analogy to wavelength modulation, if the acoustic modulation frequency is swept equally to either side of the peak of the acoustic resonance, a sweep frequency of $\omega$ will result in an amplitude modulation at a frequency of $2\omega$ since the sweep will cross the resonance center twice during every sweep cycle. When the frequency sweep is symmetric about the acoustic resonance line center, the carrier, the $2\omega$ and higher even harmonic signals will be at maximum and the $1\omega$ and higher odd harmonic signals will have zero crossings. Thus, an odd harmonic of the frequency modulation sweep rate can be used as an error signal for adjusting the frequency modulation carrier frequency. As the acoustic resonance frequency drifts with temperature, gas composition, etc., the acoustic modulation frequency will be continually updated and maintained to match the cell acoustic resonance frequency.

The present invention for acoustic resonance frequency locking can be used to equal effectiveness regardless of the method of producing photoacoustic signals. In traditional PAS the optical source radiation is amplitude modulated (AM). The modulation can be achieved by means of a mechanical chopper, a shutter, an acousto-optic modulator, or modulation of a (e.g., semiconductor) pump waveform. Other methods for achieving an amplitude modulated optical source are contemplated by and fall within the invention. In addition, Southwest Sciences, Inc. has implemented wavelength modulation spectroscopy (WMS) with PAS detection, as described in U.S. patent application Ser. No. 09/687,408. With WMS, the optical radiation source is modulated in wavelength, not amplitude (if WMS is implemented with injection current modulation of a diode laser, AM results only as a side-effect). Nevertheless, WMS produces a synchronous amplitude modulated pressure wave at the microphone. Because the present acoustic resonance frequency locking mechanism depends on features of the cell acoustic resonance and not the source of the sound, it is equally applicable to AM and WMS-based PAS.

A source of acoustic power independent of PAS generation (a speaker) has previously been used to implement an acoustic frequency locking mechanism. M. W. Sigrist and coworkers generated sound at a resonance frequency of a PAS cell with a speaker whose frequency was locked to a cell resonance via the microphone's detection phase at the resonance frequency. G. Z. Angeli, et al., "Design and characterization of a windowless resonant photoacoustic chamber equipped with resonance locking circuitry" *Rev. Sci. Instrum.* 62, 810 (1991). The locked resonance frequency was used to generate an amplitude modulated optical frequency for PAS generation The optical source modulation operated at a separate cell resonance that was a constant fraction of the frequency used for resonance locking. Several disadvantages of this approach are readily apparent. The method requires a separate acoustic source independent of the PAS generation source. The method introduces sound at frequencies other than that where the PAS signal occurs. This sound must be attenuated in order to prevent overloading of the detection microphone. Depending on the acoustic source spectral purity, noise may be induced at the PAS detection frequency. The method relies on the PAS resonance frequency and the acoustic source generated locking frequency changing in the same way in a dynamic environment. If the cell geometry changes differently for the two frequencies (due, for example, to a mechanical stress), the frequency ratio will not be constant and the lock will be lost.

M. W. Sigrist and coworkers also implemented a type of acoustic resonance maintenance by scanning over the cell resonance. A. Thony, et al., "New Developments in $CO_2$-Laser Photoacoustic Monitoring of Trace Gases ", *Infrared Phys. Technol.* 36, 585 (1995). Their method consisted of a slow scan of several discrete steps over the cell resonance. The PAS signal vs. acoustic frequency was fit to an inverted parabolic curve and the peak of the fit used as the resonance line center. The acoustic modulation frequency was then corrected to coincide with the calculated resonance line center. This method was then repeated approximately every 20 minutes. Obviously, this is not a real-time resonance frequency lock. If the cell resonance drifted during the 20 minute interval between measurements, the PAS source modulation frequency would not correspond to the cell resonance frequency. In addition, sample signal acquisition is halted during the resonance scan measurement and fitting. Continuous sample measurement is precluded in this approach. The method has utility is removing very slow drift effects, but does not provide high-fidelity resonance locking for a dynamically changing PAS sample environment. Contrast that with the present invention, whereby continual modulation over the cell resonance provides a real-time error signal for perpetual operation on the cell resonance with continuous PAS sample analysis.

SUMMARY OF THE INVENTION
(DISCLOSURE OF THE INVENTION)

The invention is of a photoacoustic spectroscopy method and apparatus for maintaining an acoustic source frequency on a sample cell resonance frequency comprising: providing an acoustic source to the sample cell, the acoustic source having a source frequency; detecting the acoustic power within the cell; repeatedly and continuously sweeping the source frequency across the resonance frequency at a sweep rate; and employing an odd-harmonic of the source frequency sweep rate to maintain the source frequency sweep centered on the resonance frequency. In the preferred embodiment, sound is generated from absorption of optical power by a species inside the sample cell, preferably frequency or wavelength modulated optical power. The invention can be employed with a flowing gas absorber species. Alternatively, sound may be generated from a speaker. A metric proportional to acoustic power inside the cell (and also to concentration of the absorber gas species) is measured, such as by measuring acoustic power occurring at an even-harmonic of the sweep rate or by measuring amplitude of a frequency modulation carrier. The odd harmonic determination is preferably done via a lock-in circuit, which may incorporate digital signal processing technology. The waveform of the acoustic source frequency is preferably sine, triangle, square, or quasi-square.

The invention is also of an acoustic resonance frequency locked photoacoustic spectrometer comprising: an acoustic source repeatedly and continuously sweeping an acoustic source frequency across a resonance frequency of a sample cell at a sweep rate; and a lock-in amplifier employing an odd-harmonic of the acoustic source frequency sweep rate to maintain the acoustic source frequency (or one of its sub-harmonic frequencies) sweep centered on the resonance frequency.

A primary object of the present invention is to provide for continuous, real-time, acoustic resonance frequency locking in PAS.

A primary advantage of the present invention is that it can operate at high frequencies and can be used in measurement of flowing gaseous species.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

The present invention is of a method and apparatus for maintaining a continuous, real-time acoustic modulation frequency on a sample cell resonance of a photoacoustic spectrometer. The invention comprises:

(a) Providing a photoacoustic sample cell with its associated geometry-determined acoustic resonances. The cell incorporates a mechanism for detecting acoustic power such as a microphone;

(b) Providing an acoustic source to the photoacoustic sample cell. Such source may be the sound produced by the absorption of optical power by a species inside the photoacoustic cell. The optical power may be amplitude or wavelength modulated. Alternatively, a source separate from the photoacoustic effect, such as a speaker, can be employed to provide acoustic power to the cell;

(c) Employing a mechanism to repetitively sweep the acoustic source frequency across a photoacoustic cell acoustic resonance; and (d) Using an odd-harmonic of the acoustic source frequency sweep rate to maintain the acoustic source frequency on a photoacoustic cell resonance; using an even-harmonic of the acoustic source frequency sweep rate as a metric proportional to the acoustic power inside the photoacoustic cell. Alternatively, the amplitude of the carrier of the frequency modulation can be used as the photoacoustic signal metric.

The invention provides a commercially-viable solution for a resonant photoacoustic spectrometer for trace gas detection. The performance of the acoustic resonance locked spectrometer is superior to devices where the acoustic modulation frequency is allowed to deviate from the cell acoustic resonance. A resonant PAS cell according to the invention allows for operation with a flowing gas sample. In order to provide comparable signal-to-noise ratios to our design, a non-resonant cell would have to operate at substantially lower frequencies where flowing gas samples are precluded.

The invention improves photoacoustic spectroscopy using resonant acoustic cells by providing acoustic resonance frequency stabilization (resonance frequency locking). Resonance frequency locking is critical when the local speed of sound varies or the cell dimensions change. Variation in the local speed of sound can occur by temperature drifts and transients caused, for example, by someone walking by the photoacoustic spectrometer. As an additional example, varying temperature is encountered in measurements of atmospheric gas (such as water vapor) on weather balloons. Changes in sample gas composition can also affect the local speed of sound (e.g., humid air has a different speed of sound than dry air). Thus, for continuous monitoring in a resonant photoacoustic spectrometer with a variable gas sample, resonance frequency locking is an enabling technology.

Figure 1:
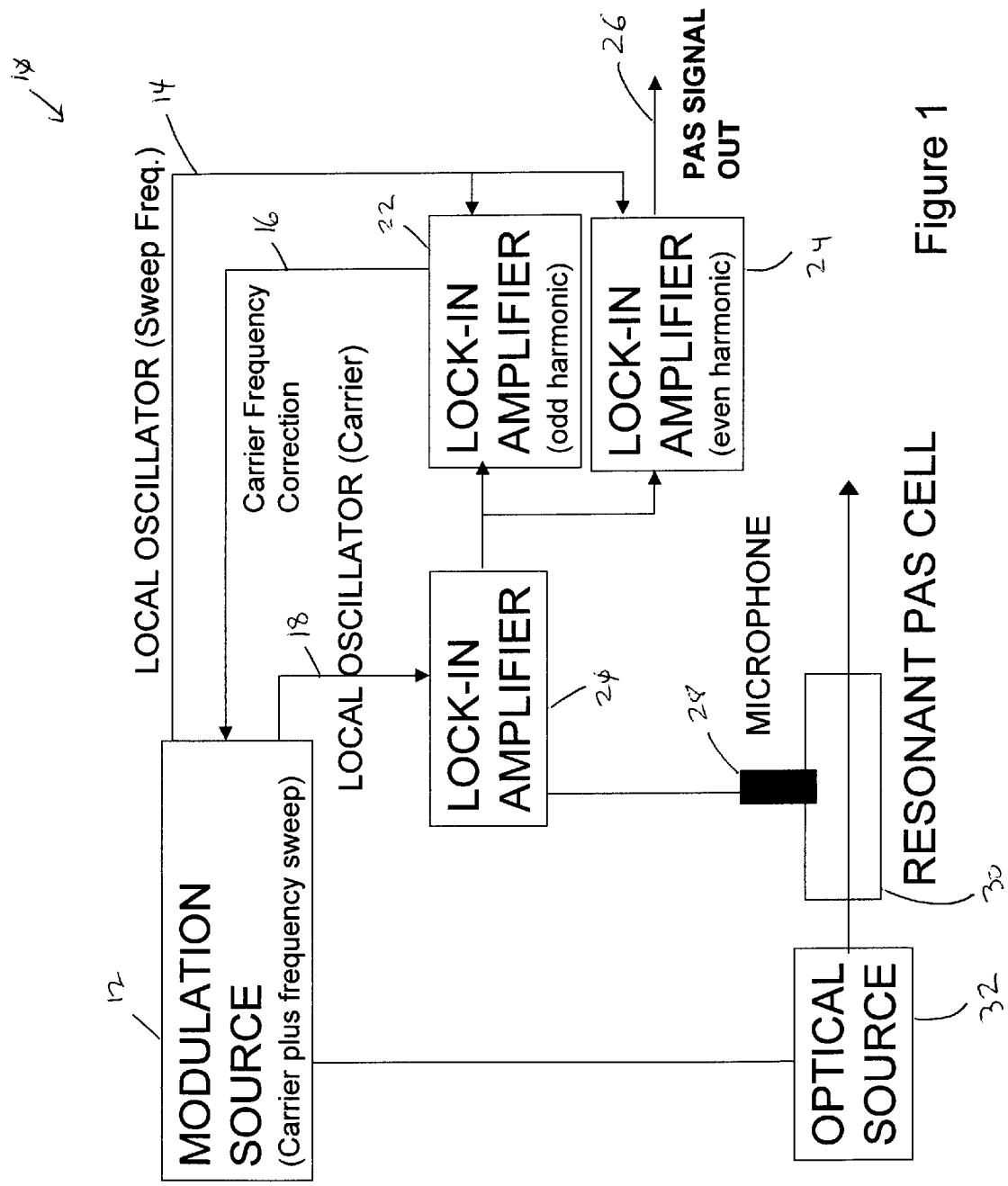
FIG. 1 is a schematic diagram of the preferred embodiment of the invention.

The preferred embodiment of the present invention 10 is shown schematically in FIG. 1. An optical source 32 is directed into a photoacoustic cell 30. The cell may be of any size or shape. It should be recognized that for any cell, there will be a set of characteristic resonance frequencies. It is preferred to employ cylindrically symmetric cells for maximum enhancement of radial and longitudinal acoustic resonances. However, other types of resonances (azimuthal, Helmholtz, etc.) and combinations or overtones of resonances are contemplated by the present invention. The optical source in FIG. 1 is modulated so as to provide a periodic heating of the gaseous sample contained within the photoacoustic cell. The modulated heating generates a sound wave that is detected using a microphone 28. The invention preferably includes modulation source (carrier plus frequency sweep) 12, which generates local oscillator (sweep frequency) 14 and local oscillator (carrier) 18, lock-in amplifier 20, lock-in amplifier 22 generating carrier frequency correction 16, and lock-in amplifier 24 generating PAS signal out 26.

The frequency of the acoustic source (acoustic source frequency) is repetitively swept across the acoustic resonance. That is, the frequency of the modulation is itself scanned over the resonance with its own well defined frequency and amplitude. This is an acoustic analog to the well-known frequency modulation of an optical carrier in FM spectroscopy or a radio frequency carrier in FM radio. However, besides being at much lower carrier frequencies than these other techniques, the present invention exploits the frequency dependent amplification of the acoustic resonance.

Consider for example a photoacoustic spectrometer system where the optical source is modulated (wavelength or amplitude) on the center (peak) of a cell acoustic resonance at 10 kHz. A sweep of the acoustic source frequency is introduced with limits of 9.9 kHz and 10.1 kHz. The sweep ($\omega$) between these limits occurs at 100 Hz. That is, the acoustic modulation frequency is swept from 9.9 kHz to 10.1 kHz and back 100 times per second. Because the cell acoustic resonance peak is at 10 kHz, it is crossed twice for each cycle of the sweep. Thus, an amplitude modulated signal is produced at 200 Hz or twice the sweep frequency ($2\omega$). When the sweep limits are symmetric around the resonance center, the signal obtained by measuring the carrier at 200 Hz will be a maximum as will be the case with other higher even harmonics of the sweep frequency. Concurrently, the signal obtained by measuring the carrier at 100 Hz ($1\omega$) will experience a zero crossing as will be the case with other higher odd harmonics of the sweep frequency. However, if the sweep limits are asymmetric around the resonance center (by shifting the carrier away from 10 kHz, or more importantly by shifting the cell resonance peak from 10 kHz by changing the local speed of sound or the cell dimensions change) the signals obtained at $2\omega$ and higher even harmonics will decrease in amplitude and the signals obtained at $1\omega$ and higher odd harmonics will increase in amplitude for small displacements from resonance center. The sign of the signals obtained at odd harmonics is dependent on the direction of imbalance in the sidebands (i.e., whether the higher frequency side band is of greater amplitude than the lower frequency sideband or vice versa). Thus, the amplitude and sign of an odd harmonic signal provide the magnitude and direction respectively for correction (if necessary) of the acoustic modulation frequency so that it is maintained to match the center of the cell acoustic resonance. The amplitude of a signal obtained at an even harmonic can be used as a measure of the photoacoustic signal amplitude. The carrier amplitude can also be used directly as a measure of the photoacoustic signal strength.

An advantage of this locking mechanism is the ready availability of small discrete lock-in integrated circuits capable of measuring photoacoustic signal at the optical source modulation frequency (and its harmonics) and at the sweep frequency (and its harmonics). Here the resonance frequency locking is dependent on a particular odd harmonic signal magnitude, not a phase measurement. Because a signal measurement may be very sensitive, it will be possible to achieve a high-fidelity lock using this method. That is, only minor frequency deviations from resonance center will occur using this locking mechanism. Thus, photoacoustic cells with very narrow resonances can be utilized to good effect with this locking mechanism. The narrower a photoacoustic resonance is, for the same frequency, the more enhancement in signal is provided. The present invention allows locking to a nearly arbitrarily narrow acoustic resonance. In addition, because the invention-preferably measures the difference in signal from both on and off the resonance peak (using an even harmonic as the PAS metric), it will suppress any signal offsets due to baseline drift.

Figure 2:
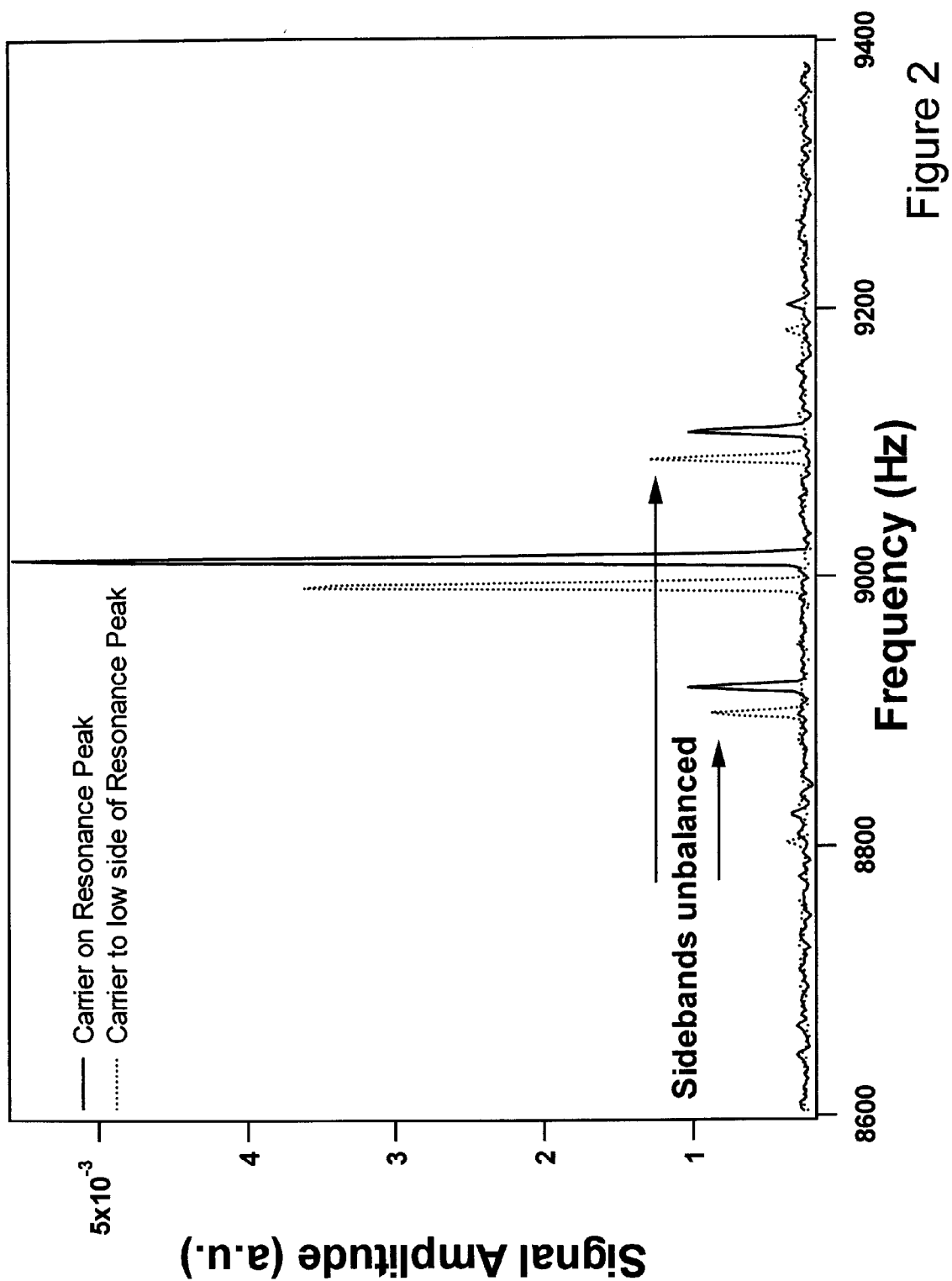
FIG. 2 shows an electronic frequency spectrum analysis of the microphone output when repetitively sweeping the acoustic modulation frequency across the cell first radial acoustic resonance at 9014 Hz when the carrier frequency is 1) coincident with and 2) to the low frequency side of the center frequency of the radial resonance. In case 1) the equal sideband amplitudes provide a zero value of the odd sweep rate harmonics while the even harmonics are at individual maxima. In case 2) the unequal sideband amplitudes produce a non-zero value for the odd harmonics which dictates the direction and magnitude of a frequency correction (error signal) to adjust the acoustic carrier frequency to be centered on the cell acoustic radial resonance.

FIG. 2 shows frequency spectra as measured by an electronic spectrum analyzer when using the preferred embodiment to modulate a light emitting diode (LED). The low frequency modulation of the carrier frequency (S) introduces frequency side bands spaced by integer multiples of T, the sweep frequency (95 Hz), from the carrier at 9014 Hz. In the first case the carrier is exactly centered on the cell acoustic resonance at 9014 Hz and the side bands are of equal amplitude. Because the side bands are of equal amplitude they provide the same beat signal with the carrier frequency but differ in phase by 180 degrees. Thus, demodulating the microphone output at odd harmonics of the sweep frequency produces zero net signal due to destructive interference. Conversely, the signals obtained by demodulating the microphone output at even harmonics are at maxima due to constructive interference. In the second case of FIG. 2 the carrier is slightly off center, at 8992 Hz, of the cell acoustic resonance. Now the frequency sidebands do not have equal amplitudes. These beat signals do not completely cancel due to destructive interference for the odd harmonics and the resulting signals obtained from the lock-in amplifier are non-zero. The odd harmonic signals are linear with the carrier frequency displacement from the center of the acoustic resonance for small displacements, thus providing an error signal for resonance frequency locking.

It should be appreciated that there are various modulation waveforms available to sweep the optical source modulation frequency or its harmonics across the cell acoustic resonance. These include sine, triangle, square, quasi-square, etc. This list is not meant to be exhaustive and other arbitrary waveforms are contemplated by the invention. Some waveforms are capable of enhancing the signal from certain harmonics. For example, square wave modulation enhances odd harmonics at the expense of the even harmonics.

Digital signal processors (DSP) are capable of providing arbitrarily complex modulation and demodulation waveforms. The use of DSP technology to acquire and process the photoacoustic signal is contemplated by the invention. It should be noted that DSP technology can obviate the need for multiple discrete lock-ins.

When PAS is implemented with wavelength modulation methods, the present invention for acoustic resonance frequency locking can be used simultaneously with other line locking methods for constraining the optical source wavelength on a gaseous absorption feature. The sweep of the acoustic modulation frequency will not impede the ability of a lock-in using an optical detector to maintain the optical source wavelength on the center of the target species absorption center. This combination of absorption resonance line locking with acoustic resonance frequency locking is contemplated by the present invention.

Industrial Applicability

The invention is further illustrated by the following non-limiting examples.

EXAMPLE 1

Amplitude Modulation. A 1380 nm broadband light emitting diode (LED) was used as the optical source. Amplitude modulation was achieved by 100% square wave modulating the injection current to the LED. Thus, the LED was turned on and off at the injection current modulation frequency. Using a nominal 2" inner diameter cylindrical cell, the first radial resonance was determined to be around 8800 Hz. The acoustic signal was generated by moisture absorption in this wavelength region. The present invention for continuous, real-time locking of the acoustic carrier frequency was used to lock the modulation frequency to the center of the cell acoustic resonance as the moisture content of the air was raised.

EXAMPLE 2

Wavelength Modulation. A 1392.5 nm single mode distributed feed back (DFB) diode laser was used as the optical source. The laser was utilized to detect moisture. Wavelength modulation was implemented by modulating the laser injection current. DFB lasers scan nearly linearly in wavelength with injection current. The modulation frequency was at one half the first radial resonance frequency, around 4400 Hz, and detected at 2 f or 8800 Hz. When the laser wavelength was on the line center of the moisture absorption, sound was produced at 2 f which was enhanced by the acoustic cell resonance. Acoustic resonance locking was implemented using the present frequency modulation method. Also, wavelength modulation of the DFB laser was achieved directly at 8800 Hz and detected at 1 f.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A photoacoustic spectroscopy method for maintaining an acoustic source frequency on a sample cell resonance frequency, the method comprising the steps of:
  providing an acoustic source to the sample cell, the acoustic source having a source frequency;
  repeatedly and continuously sweeping the source frequency across the resonance frequency at a sweep rate; and
  employing an odd-harmonic of the source frequency sweep rate to maintain the source frequency sweep centered on the resonance frequency.

2. The method of claim 1 wherein the providing step comprises generating sound from absorption of optical power by a species inside the sample cell.

3. The method of claim 2 wherein generating sound from absorption of optical power comprises absorption of optical power modulated by one or more modulating steps selected from the group consisting of amplitude modulating and wavelength modulating.

4. The method of claim 2 wherein generating sound comprises generating sound from absorption of optical power by a flowing gas species.

5. The method of claim 1 wherein the providing step comprises generating sound from a speaker.

6. The method of claim 1 additionally comprising the step of measuring a metric proportional to acoustic power inside the cell.

7. The method of claim 6 wherein the measuring step comprises measuring variations in said metric occurring at an even harmonic of the sweep rate.

8. The method of claim 6 wherein the measuring step comprises measuring amplitude of a carrier frequency.

9. The method of claim 6 wherein in the measuring step the metric is also proportional to a concentration of a species inside the sample cell.

10. The method of claim 1 wherein the employing step comprises using a lock-in circuit referenced to an odd harmonic of the sweep rate.

11. The method of claim 10 wherein in the employing step the lock-in circuit comprises digital signal processing means.

12. The method of claim 1 wherein in the sweeping step a waveform of the acoustic source frequency is selected from the group consisting of sine, triangle, square, and quasi-square.

13. A photoacoustic spectroscopy apparatus for maintaining an acoustic source frequency on a sample cell resonance frequency, said apparatus comprising:

means for providing an acoustic source to the sample cell, said acoustic source having a source frequency;

means for repeatedly and continuously sweeping the acoustic source frequency across the resonance frequency at a sweep rate; and means for employing an odd-harmonic of the acoustic source frequency sweep rate to maintain the acoustic source frequency sweep centered on the resonance frequency.

14. The apparatus of claim 13 wherein said providing means comprises means for generating sound from absorption of optical power by a species inside the sample cell.

15. The apparatus of claim 14 wherein said means for generating sound from absorption of optical power comprises means for generating optical power modulated by one or more modulations selected from the group consisting of amplitude modulation and wavelength modulation.

16. The apparatus of claim 14 wherein said means for generating sound comprises means for generating sound from absorption of optical power by a flowing gas species.

17. The apparatus of claim 13 wherein said providing means comprises a speaker.

18. The apparatus of claim 13 additionally comprising means for measuring a metric proportional to acoustic power inside the cell.

19. The apparatus of claim 18 wherein said measuring means comprises means for measuring variations in said metric occurring at an even harmonic of the sweep rate.

20. The apparatus of claim 18 wherein said measuring means comprises means for measuring amplitude of a carrier frequency.

21. The apparatus of claim 18 wherein in said measuring means the metric is also proportional to a concentration of a species inside the sample cell.

22. The apparatus of claim 13 wherein said employing means comprises using a lock-in circuit referenced to an odd harmonic of the sweep rate.

23. The apparatus of claim 22 wherein said lock-in circuit comprises digital signal processing means.

24. The apparatus of claim 13 wherein in said sweeping means comprises means for generating a waveform of the acoustic source frequency selected from the group consisting of sine, triangle, square, and quasi-square.

25. An acoustic resonance frequency locked photoacoustic spectrometer comprising:

an acoustic source repeatedly and continuously sweeping an acoustic source frequency across a resonance frequency of a sample cell at a sweep rate; and a lock-in amplifier employing an odd-harmonic of the acoustic source frequency sweep rate to maintain the acoustic source frequency sweep centered on the resonance frequency.

* * * * *